United States Patent [19]

Vanderspurt et al.

[11] 4,269,781

[45] May 26, 1981

[54] DIMERIC CARBONYLATION OF 1,3-BUTADIENE

[75] Inventors: Thomas H. Vanderspurt, Stockton; Paul M. Zema, Kenilworth, both of N.J.

[73] Assignee: Celanese Corporation, New York, N.Y.

[21] Appl. No.: 119,683

[22] Filed: Feb. 8, 1980

[51] Int. Cl.³ ............................................. C11C 3/02
[52] U.S. Cl. ......................................... 260/410.9 R
[58] Field of Search ............... 260/410.6, 410.9 C; 560/233

[56] References Cited

U.S. PATENT DOCUMENTS

| | | | |
|---|---|---|---|
| 3,780,074 | 12/1973 | Romanelli | 260/410.9 C |
| 4,041,057 | 8/1977 | Fanning | 260/410.9 C |

*Primary Examiner*—John F. Niebling
*Attorney, Agent, or Firm*—Kenneth A. Genoni

[57] ABSTRACT

This invention involves a process for dimeric carbonylation of 1,3-butadiene in the presence of an alkanol and a palladium-phosphine complex catalyst to yield alkyl nonadienoate.

An important aspect of the invention process is the recovery of a separate alkanol-rich liquid phase which contains the catalyst in a highly reactive form suitable for recycle.

32 Claims, No Drawings

DIMERIC CARBONYLATION OF 1,3-BUTADIENE

BACKGROUND OF THE INVENTION

Catalytic carbonylation of olefinic and acetylenic compounds to form oxygenated derivatives with an increased content of carbon atoms is a well-established technology. Various developments and improvements are described in U.S. Pat. Nos. such as 2,876,254; 3,040,090; 3,455,989; 3,501,518; 3,507,891; 3,652,655; 3,660,439; 3,700,706; 3,723,486; 3,746,747; 3,755,419; 3,755,421; 3,793,369; 3,856,832; 3,859,319; 3,887,595; 3,952,034; 3,992,423; and references cited therein.

Of particular interest with respect to the present invention is the chemical literature relating to dimeric carbonylation of aliphatic conjugated dienes in the presence of a hydroxylated coreactant and a catalyst complex of a Group VIII noble metal and a Group VB tertiary donor ligand. The dimeric carbonylation reaction is illustrated by the following chemical equations with respect to the interaction of 1,3-butadiene with water and with alkanol:

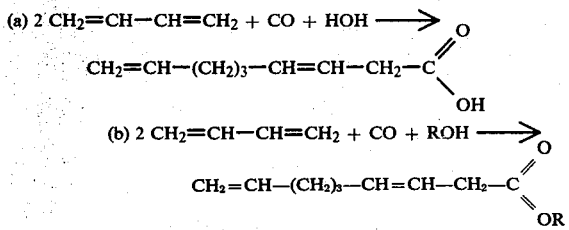

In a report published in Tetrahedron, 28, 3721 (1972), there is described a dimeric carbonylation of 1,3-butadiene in the presence of alkanol and a palladium-phosphine complex catalyst to yield alkyl 3,8-nonadienoate. The publication discloses that the absence of halide coordinated to the palladium metal is essential for the formation of alkyl nonadienoate product. In the presence of halide, one mole of 1,3-butadiene reacts with one mole of carbon monoxide and one mole of alkanol to yield alkyl 3-pentenoate.

U.S. Pat. No. 4,124,617 describes a process for the selective production of fatty acid derivatives from aliphatic diene substrates, in the presence of dual-function homogeneous palladium complexes and certain classes of organic tertiary nitrogen bases. One disadvantage of this type of process is that the use of tertiary nitrogen bases promotes the production of unwanted byproducts such as C$_5$-esters.

In processes for dimeric carbonylation of aliphatic conjugated dienes such as are disclosed above, the dimeric product is separated from the catalyst complex and other components of the reaction product mixture employing conventional techniques such as distillation. Such product recovery procedures have the disadvantage that some of the catalyst complex (e.g., palladium-phosphine complex) is lost by precipitation, and more significantly, the catalyst complex invariably suffers from a loss of reactivity. This is a serious consequence for purposes of a catalyst complex which is intended to be recovered and recycled in a dimeric carbonylation process.

Accordingly, it is a main object of this invention to provide an improved process for conversion of aliphatic conjugated dienes into fatty acid derivatives.

It is another object of this invention to provide a process for producing alkyl nonadienoate and nonadienoic acid by dimeric carbonylation of 1,3-butadiene with improved conversion and selectivity.

It is a further object of this invention to provide a process for producing alkyl 3,8-nonadienoate and alkyl 2,8-nonadienoate by dimeric carbonylation of 1,3-butadiene with carbon monoxide and alkanol in the presence of palladium-phosphine complex catalyst, wherein said catalyst is recovered from the process with essentially no loss of catalytic reactivity and selectivity properties.

Other objects and advantages of the present invention shall become apparent from the accompanying description and illustrative processing data.

DESCRIPTION OF THE INVENTION

One or more objects of the present invention are accomplished by the provision of a process for producing and recovering alkyl nonadienoate which comprises the steps of (1) reacting 1,3-butadiene with carbon monoxide and a water-soluble alkanol containing between about 0.5–10 weight percent of water, in the presence of a catalyst complex of palladium and tertiary phosphine ligand, to yield a liquid phase product mixture containing alkyl nonadienoate; (2) contacting the product mixture with a hydrocarbon solvent to form two liquid phases; and (3) separating the two liquid phases, and recovering alkyl nonadienoate from the hydrocarbon solvent phase.

In one of its embodiments, this invention more particularly provides a process for producing and recovering alkyl nonadienoate which comprises the steps of (1) reacting butadiene with at least molar equivalents of carbon monoxide and water-soluble alkanol in the presence of a hydrocarbon solvent and a catalytic quantity of a complex of palladium and tertiary phosphine ligand, at a temperature between about 30° C. and 150° C. and a pressure between about 200 and 3000 psi, to yield a reaction mixture containing alkyl nonadienoate; (2) adjusting the relative quantities of hydrocarbon solvent and alkanol in the reaction mixture, and adding water as required, sufficient to provide a hydrocarbon solvent phase and an alkanol phase containing between about 0.5–10 percent of water; and (3) separating the two phases and recovering alkyl nonadienoate from the hydrocarbon solvent phase.

The alkanol coreactant employed in the process is preferably selected from water-soluble alkanol compounds which are miscible with water in all proportions. Suitable water-soluble alkanols include those containing between 1 and about 5 carbon atoms and between 1 and about 4 hydroxyl groups. Illustrative of suitable water-soluble alkanols are methanol, ethanol, ethylene glycol, propanol, glycerine, 1,4-butanediol, pentaerythritol, and the like.

When the first step dimeric carbonylation reaction is completed, and at the time when the water-soluble alkanol phase and the hydrocarbon solvent phase are to be separated, it is essential that the alkanol phase contains between about 0.5–10 weight percent of water. This is required in order to effect an efficient partition of the alkyl nonadienoate and other conversion products into the hydrocarbon phase, and the catalyst complex into the alkanol phase. If the alkanol phase contains in addition an unreactive water-soluble diluent such as acetonitrile or tetrahydrofuran, then the 0.5–10 weight percent water content is based on the combined weight of the water-soluble components.

The water-soluble alkanol coreactant is employed in the process in a quantity which at least satisfies the stoichiometric requirements of the dimeric carbonylation reqction, i.e., at least one mole of alkanol per two moles of 1,3-butadiene. In a process embodiment in which the water-soluble alkanol also functions as a liquid phase reaction medium, then the water-soluble alkanol is employed in a large excess in comparison with the quantity of 1,3-butadiene being reacted, e.g., between about 5–100 moles of alkanol per mole of 1,3-butadiene.

Likewise, the carbon monoxide coreactant is employed in a quantity which at least satisfies the stoichiometry of the process. It is preferred that the carbon monoxide is introduced into the process reaction system up to a partial pressure of between about 100 and 1000 psi of carbon monoxide. The carbon monoxide environment in the process system can contain one or more inert gases such as nitrogen, helium, argon, and the like. For optimal results it is essential that the process is conducted in a deoxygenated environment, so as not to affect adversely the 1,3-butadiene conversion rate and the selective yield of alkyl nonadienoate product.

The hydrocarbon solvent employed in the invention process is preferably selected from acyclic and cyclic paraffins containing between 3 and about 8 carbon atoms. Illustrative of preferred hydrocarbon solvents are propane, butane, pentane, cyclopentane, hexane, cyclohexane, heptane and octane. Petroleum refinery light hydrocarbon mixtures are suitable for use as the hydrocarbon solvent in the process.

The hydrocarbon solvent is employed in a quantity which is at least sufficient to facilitate the efficient partitioning of the product and catalyst components between the hydrocarbon solvent phase and water-soluble alkanol phase, before the two phases are separated in step (3) of the invention process. The upper limit of the quantity of hydrocarbon solvent used is dictated by practical considerations of equipment design and energy requirements.

Another important aspect of the present invention process is the presence of a catalyst which is highly selective for dimeric carbonylation of aliphatic conjugated diene compounds. A highly preferred catalyst is one which is a complex of palladium and a tertiary phosphine donor ligand.

The term "phosphine" is meant to include corresponding phosphite derivatives. Illustrative of suitable tertiary phosphine ligands are triisopropylphosphine, tri-n-butylphosphine, triisobutylphosphine, tri-n-octylphosphine, triphenylphosphine, tritolylphosphine, tribenzylphosphine, and the corresponding phosphite compounds. The substituents in the tertiary phosphine ligands can be the same or different, and mixtures of tertiary phosphine ligands can be employed. Illustrative of a ligand mixture is one containing about 70–99 mole percent trialkylphosphine (e.g., triisopropylphosphine) and about 1–30 mole percent triarylphosphine (e.g., triphenylphosphine). A preferred class of tertiary phosphine ligands are trialkylphosphines in which each alkyl group contains between 2 and about 8 carbon atoms.

A unique aspect of the present invention is based on the discovery that a specific type of palladium/tertiary phosphine complex catalyst appears to exhibit a superior combination of properties with respect to dimeric carbonylation of 1,3-butadiene in comparison with a complex of palladium and some other tertiary phosphine ligand, i.e., the preferred catalyst contains a trialkylphosphine ligand which has a $\Delta$HNP basicity between about 70–350 and a steric parameter $\theta$ between about 136°–190°. Illustrative of this category of trialkylphosphines are triisopropylphosphine, tri-secondary-butylphosphine and triisobutylphosphine.

For example, palladium/triisopropylphosphine complex provides a better balance of conversion and selectivity as a catalyst in the present invention dimeric carbonylation of 1,3-butadiene process than does any of palladium/tri-n-propylphosphine complex, palladium/tri-n-butylphosphine complex, palladium/diethylphenylphosphine complex, palladium/tricyclohexylphosphine complex, or palladium/triphenylphosphine complex, respectively.

By the term "$\Delta$HNP" is meant the difference in the half neutralization potential between the ligand under consideration and N,N'-diphenylquanidine as determined in accordance with the procedure described in Analytical Chemistry, 32, 985–987 (1960). The $\Delta$HNP of 24 tertiary phosphines are listed in U.S. Pat. No. 3,527,809.

By the term "steric parameter $\theta$" is meant the apex angle of a cylindrical cone, centered 2.28 Å from the center of the phosphorus atom, which touches the Van der Waals radii of the outermost atoms of the isopropyl substituents [C. A. Tolman, J. Amer. Chem. Soc., 92, 2953 (1970); Ibid, 92, 2956 (1970); and Ibid, 96, 53 (1974)].

It appears that the superior catalytic properties of a palladium/triisopropylphosphine type of catalyst complex are attributable to the specifically inherent basicity and steric structure of triisopropylphosphine as a complexing ligand. It is believed that the physicochemical properties of triisopropylphosphine favor the formation of a highly active ·m of complexed palladium catalyst for the purposes oı .ımeric carbonylation of 1,3-butadiene.

A methanolic solution of palladium/triisopropylphosphine (¼) under one or more atmospheres of carbon monoxide exhibits the following characteristics when examined by $P^{31}$ NMR. No $AB_2$ pattern is apparent, but a rapid exchange between the palladium and phosphine is observed. IR examination of the solution indicates some evidence of a $Pd.(CO).(PR_3)_3$ complex species.

By comparison, tri-n-butylphosphine and tri-n-propylphosphine at the same palladium/phosphine molar ratio (¼) each show a clear $AB_2$ pattern.

Under comparative conditions in the practice of the present invention dimeric carbonylation of 1,3-butadiene process (e.g., 110° C. and 750 psig), there is essentially no induction period in the presence of a palladium/triisopropylphosphine complex catalyst, and there is a relatively long reduction period (e.g. 45 minutes) when the phosphine ligand in the catalyst is either tri-n-propylphosphine or tri-n-butylphosphine. The observed long induction period decreases as the ratio of phosphine to palladium decreases. However, the risk of palladium metal deposit increases as the ratio of phosphine to palladium decreases.

The palladium-phosphine complex catalyst employed in the practice of the dimeric carbonylation reaction step of the present invention process normally will contain between about 2 and 8 moles of tertiary phosphine ligand per gram atom of palladium metal. A larger excess of ligand may be employed if desired.

The palladium-phosphine complex can be prepared prior to its use in the operation of the reaction system, in accordance with catalyst preparative methods described in the chemical literature [e.g., J. Chem. Soc., 3632 (1965)].

Alternatively, the palladium and tertiary phosphine components of the catalyst can be introduced separately into the reaction system where they combine to form the catalyst complex in situ. The palladium precursor compound is preferably in the form of a palladium-containing salt, such as palladium acetate, palladium propionate, palladium acetylacetonate, palladium nitrate, and the like.

It is highly preferred that the dimeric carbonylation step of the invention process is conducted in the presence of a vinyl polymerization inhibitor, e.g., hydroquinone. If an inhibitor is not included in the reaction system then there is an increased incremental loss of 1,3-butadiene to polymeric byproducts.

The temperature for the first step dimeric carbonylation reaction can vary in the range between about 30° C. and 200° C., and preferably in the range between about 50° C. and 140° C.

The pressure in the first step reaction zone can vary in the range between about 200 and 3000 psi, and preferably in the range between about 300 and 1500 psi. As previously mentioned, it is advantageous to provide a carbon monoxide partial pressure in the range between about 100 and 1000 psi in the first step reaction zone.

In a typical batch type process, the reaction time for the dimeric carbonylation step will average in the range between about 2 and 20 hours, as determined by temperature and pressure parameters and the reactivity of the palladium-phosphine complex catalyst.

It has been found that the catalyst reactivity remains stable if it is maintained in contact with 1,3-butadiene or carbon monoxide during all phases of the invention process. For this reason there is advantage in a batch type process to convert less than 100 percent of the 1,3-butadiene substrate during the dimeric carbonylation reaction step. Also, insofar as it is practical, during the alkyl nonadienoate product recovery and catalyst recovery and recycle procedures it is highly advantageous to maintain the catalyst-containing alkanol phase in contact with an atmosphere of 1,3-butadiene and/or carbon monoxide.

When a polymerization inhibitor is employed in the present invention process, and other precautions mentioned above are observed, the yield of byproducts can be limited to less than about 10 percent. The byproducts produced during the 1,3-butadiene dimeric carbonylation reaction step include 3-pentenoic acid; alkyl 3-pentenoate; vinylcyclohexene; 1,3,7-octatriene; 1-methoxy-3,7-octadiene; and oligomeric polyenes.

In a batch-type process this invention readily provides a 1,3-butadiene conversion between about 80–100 percent, and a selectivity to alkyl nonadienoate and nonadienoic acid of at least 80 mole percent, based on the total moles of conversion products.

In the process embodiment described above in which the step (1) dimeric carbonylation reaction system contains both alkanol and hydrocarbon solvent, it is highly preferred that the proportions of alkanol and hydrocarbon solvent are such that the 1,3-butadiene conversion proceeds in a substantially homogeneous liquid phase reaction medium. After the step (1) reaction is completed, the liquid reaction product mixture is cooled to room temperature or lower. As required, the relative quantities of the alkanol and hydrocarbon solvent components are adjusted, and water is added, to achieve separation of the reaction medium into an alkanol phase and a hydrocarbon solvent phase.

Any high molecular weight polyene byproducts in the reaction product mixture tend to precipitate out during the cooling and phase separation procedures. As necessary, the reaction product mixture can be filtered to remove polymeric precipitate.

The hydrocarbon solvent phase contains alkyl nonadienoate and substantially all of the organic byproducts. In one procedure, the hydrocarbon solvent is flashed off and recycled in the process, and the alkyl nonadienoate product is recovered and purified by conventional chemical or physical techniques. Byproducts such as octatriene and methoxyoctadiene can be recycled to step (1) of the process where they can be converted to alkyl nonadienoate.

The alkanol phase which is recovered during the liquid phase separation step contains the palladium-phosphine complex catalyst, and is recycled to step (1) of the process.

During the phase separation step, the components of the product reaction mixture are partitioned between the alkanol and hydrocarbon solvent phases as determined by the respective solubility characteristics of the components. The hydrocarbon solvent phase contains an equilibrium quantity of alkanol soluble components, and the alkanol phase contains an equilibrium quantity of hydrocarbon solvent soluble components. Preferably, the hydrocarbon solvent phase is extracted with fresh alkanol, and the alkanol phase is extracted with fresh hydrocarbon solvent, before each of the said phases is subjected to the subsequent procedures. The respective extract aliquots can be processed in an appropriate manner to salvage alkyl nonadienoate product and palladium-phosphine complex catalyst.

The foregoing description is essentially concerned with batch type practice of the invention process. In another embodiment, this invention contemplates a continuous process for producing and recovering alkyl nonadienoate which comprises the step of (1) continuously charging and substantially filling an elongated reactor with a liquid phase reaction medium comprising water-soluble alkanol having a water content of between about 0.5–10 weight percent; (2) maintaining the reactor contents at a temperature between about 50° C. and 130° C. and under a partial pressure between about 100 and 1000 psi of carbon monoxide; (3) continuously introducing 1,3-butadiene and hydrocarbon solvent into the first end of the reactor; (4) continuously withdrawing hydrocarbon solvent as a separate phase from the second end of the reactor; (5) continuously separating alkyl nonadienoate product from the withdrawn hydrocarbon solvent phase; and (6) continuously recycling recovered hydrocarbon solvent to step (2) of the process.

Illustrative of a specific application of the above described continuous process, a solution of palladium complexes (e.g., palladium phosphine carbonyl species), water-soluble alkanol and water is fed continuously to a first reaction zone of an elongated reactor system, simultaneously with the introduction of 1,3-butadiene and a hydrocarbon solvent (e.g., a light paraffin such as hexane). In the first reaction zone, the feed materials are admixed efficiently with each other and with carbon monoxide which is present at a partial pressure of at least 100 psi (e.g., 300–1200 psi). The admixture is passed into a second reaction zone of the reactor system, in which zone there is no input of additional carbon monoxide. The temperature and flow rates are controlled in the second reaction zone so that optimal proportions of 1,3-butadiene and carbon monoxide are reacted. The presence of incremental carbon monoxide is maintained in the second reaction zone in a quantity sufficient to prevent the formation of methoxyoctadiene byproducts, but not sufficient to favor the formation of palladium poly-carbonyl and poly-palladium carbonyl complex species. The resultant reaction product mixture is cooled, and as necessary, additional alkanol and-/or hydrocarbon solvent and/or water are added to effect liquid phase separation. The hydrocarbon phase is stripped of solvent, and the solvent is recycled. The aqueous alkanol phase first is extracted with hydrocarbon solvent, and then the aqueous alkanol phase and its contents (i.e., the palladium phosphine catalyst) are recycled in the continuous process.

In one modification of the above described continuous process, the liquid phase reaction medium can comprise a mixture of water-soluble alkanol, and water-soluble diluent which is unreactive under processing conditions, e.g., acetonitrile, tetrahydrofuran, dimethylformamide, and the like. For example, the liquid phase reaction medium contained in the elongated reactor can consist of about 10–80 weight percent of water-soluble alkanol and about 10–80 weight percent of unreactive water-soluble diluent, and about 0.5–10 weight percent of water, based on the total weight of the liquid phase reaction medium.

The following examples are further illustrative of the present invention. The reactants and other specific ingredients are presented as being typical, and various modifications can be devised in view of the foregoing disclosure within the scope of the invention.

EXAMPLE I

A stirred autoclave is charged with 25 grams of methanol, 6.5 grams of tri-n-butylphosphine, 0.9 gram of palladium (II) acetate and 40 milliliters of n-pentane. The reactor is flushed twice with carbon monoxide, followed by the addition of 1,3-butadiene and sufficient carbon monoxide to provide a total reactor pressure of 800 psig.

The reactor temperature is increased to 100° C., and maintained for 24 hours. At the end of 24 hours reaction period 83% of the methanol has reacted. On a molar basis, 46.4 percent of the recovered liquid products are methyl 3,8-nonadienoate and methyl 2,8-nonadienoate.

The total liquid reaction product mixture recovered weighs 91 grams. To this product mixture is added 75 milliliters of methanol. The resultant admixture is filtered to remove about 5 grams of polymeric precipitate.

The filtered reaction product mixture is combined with about 125 grams of n-pentane and 6 milliliters of water to effect phase separation. The upper phase consists of a n-pentane solution containing some methanol and substantially all of the methyl nonadienoate product. The lower phase consists of 74% methanol, 13% n-pentane, 4% 1,3-butadiene, 4.6% methyl nonadienoate, and the balance is a mixture of other products.

The said alkanol-rich lower phase is admixed with 32 grams of n-pentane, and the resultant admixture is charged to the reactor. The reactor is flushed with carbon monoxide, 98 grams of 1,3-butadiene are added, and the reaction is pressured to 780 psig with carbon monoxide. The reaction medium is heated at 100° C. for 24 hours. After the reaction is completed, the liquid product mixture weighs about 158 grams. About 50% of the methanol has reacted, and about 3 grams of polyene byproduct is recovered. Based on the total liquid products in the product mixture, the molar selectivity to methyl nonadienoates is 76%.

When the procedure is repeated, except that the 1,3-butadiene is inhibited with 0.1% t-butylcatechol, and 0.25 gram of hydroquinone and 0.25% methyl ether of hydroquinone is included in the reaction medium, no polymer formation is observed, and conversion and selectivity are higher.

EXAMPLE II

A 300 ml stirred autoclave is charged with 50 grams of methanol, 50 grams of pentane, 5.14 grams of triisopropylphosphine, 1.8 grams of palladium acetate, 0.25 gram of hydroquinone and 0.25 gram of methyl ether of hydroquinone. The reactor is flushed with carbon monoxide to exclude oxygen, and pressurized to 300 psig carbon monoxide pressure as the temperature is increased to 100° C. At this point a 98 gram quantity of 1,3-butadiene inhibited with 0.1% t-butylcatechol is added, followed within 5 seconds by sufficient carbon monoxide to increase the total pressure to 910 psig. After 30% of the methanol has reacted (less than 2 hours), additional inhibited 1,3-butadiene and a trace of water are added at the rate of 31.5 milliliters of 1,3-butadiene and 0.05 milliliters of water per hour for four hours. During this addition period excess carbon monoxide is made available to the reactor from a storage vessel.

After the 1,3-butadiene addition is completed, the flow of carbon monoxide into the reactor is stopped. Over a 9 hour period the temperature of the reaction medium is allowed to decrease as the excess carbon monoxide in solution is being consumed. The final temperature of reaction medium is about 5° C.

The product mixture consists of two phases, an upper phase comprising the nonadienoate products in pentane, and a lower methanol-rich phase which contains substantially all of the palladium-phosphine complex catalyst as well as methyl pentenoate byproduct.

Approximately 94% conversion of both methanol and 1,3-butadiene is achieved. The overall molar selectivity to the desired straight chain methyl 3,8-nonadienoate and methyl 2,8-nonadienoate is 89%. The molar selectivity to the methyl esters of branched $C_9$-carboxylic acids is about 7%.

An important feature of the above described procedure is the controlled access of carbon monoxide to the reaction system during the overall process. At the end of main reaction time, the flow of carbon monoxide into the reactor is terminated. This is followed by an extended cooling down period, during which time the residual carbon monoxide is gradually consumed. In this manner, there is obtained a two phase system in which the catalyst is contained as a soluble component of the lower methanol-rich phase.

If excess carbon monoxide is maintained in the reaction system at the end of the main reactor period, then a major portion of the palladium catalyst is converted into a form which is soluble in the upper nonadienoate phase, and therefore not readily available for recycling in the process. Recovery of the catalyst becomes difficult. Further, the reaction medium must be gradually cooled as the residual carbon monoxide is consumed to minimize side reactions and prevent the loss of desired straight chain nonadienoate products.

EXAMPLE III

This example, illustrates a present invention embodiment in which the dimeric carbonylation of 1,3-butadiene is operated on a continuous basis.

A reactor system is provided which consists of a 300 ml stirred autoclave having a bottom withdrawal line connected through a defoaming vessel to a pump. The pump apparatus is in turn connected to a coiled length of 0.5 inch tubing (approx. volume of 100 ml). The other end of the coiled tubing unit is attached to a countercurrent extraction apparatus constructed of high pressure sight gauges. The autoclave is equipped with a hollow shafted multiblade mixing turbine.

The autoclave, coiled tubing unit and feed mixing units are heated by circulating hot oil. The countercurrent extraction apparatus is maintained at a temperature between about −20° C. and −30° C., as is a mixing unit which is located between the coiled tubing unit and the extraction apparatus.

A feed solution is prepared which consists of components which are in a ratio of 27 grams of methanol to 60 grams of pentane, and which is 0.09 molar in palladium and 0.36 molar in triisopropylphosphine. The feed solution is preheated and fed into the stirred autoclave reactor. Simultaneously, 50 grams per hour of liquid 1,3-butadiene (inhibited with t-butylcatechol) is pumped into the reactor, and carbon monoxide is entered into the reactor through the hollow stirrer shaft under 750 psig pressure. The carbon monoxide consumption is about 22.4 grams per hour.

The average residence time of liquid reaction medium in the autoclave reactor unit is about one hour. The average residence time of the liquid water medium in the coiled tubing unit is about 30 minutes. Both 1,3-butadiene and carbon monoxide are consumed during the residence period of the reaction medium in the coiled tubing unit. The flow rate and other parameters are balanced so that a low level of carbon monoxide and 1,3-butadiene are present when the reaction medium reaches the end of the coiled tubing zone. A large excess of carbon monoxide at this point causes the formation of palladium poly-carbonyl (1890 cm$^{-1}$, 1875 cm$^{-1}$, and 1855 cm$^{-1}$) and poly-palladium carbonyl species (IR bands, 1900 cm$^{-1}$ and 1820 cm$^{-1}$) which are soluble in pentane, a factor which complicates the recovery and recycle of palladium catalyst during the subsequent extraction step of the process. When the carbon monoxide is maintained at a low level toward the end of the coiled tubing zone, the formation of palladium-(carbon monoxide)-(triisopropylphosphine)$_3$ complex (IR band, 1966 cm$^{-1}$) is favored. This catalyst species is solubilized in the methanol-rich phase during the extraction procedure, and facilitates catalyst recovery and recycle.

At an autoclave reaction temperature of 130° C., 90% 1,3-butadiene conversion with 92% selectivity to methyl nonadienoates is achieved. The methanol (in excess) is 50% converted with 95% selectivity to methyl nonadienoates. The production of methyl nonadienoates is at the rate of about 65 grams per hour.

The liquid product stream from the coiled tubing unit is admixed with a 17 gram per hour feed of methanol and entered into the chilled mixing section. The methanol feed contains about 5% by volume of water, to facilitate phase separation in the extraction unit.

The liquid product stream effluent from the chilled mixing section is passed into the extraction unit, and contacted countercurrently with 200 milliliters per hour of cold pentane.

The methanol-rich phase which contains dissolved catalyst is withdrawn continuously from the bottom of the extraction unit. It is blended with pentane, and as necessary, make-up palladium and triisopropylphosphine are added, and the liquid stream is recycled to the autoclave reactor zone.

The pentane solution phase which contains nonadienoate product is withdrawn continuously from the top of the extraction unit, and the pentane is flashed at 120° C. under one atmosphere of carbon monoxide. The pentane (and some methanol) is condensed and recycled to the autoclave reactor and extraction unit of the system in proportions as required.

The bottoms fraction recovered from the flash distillation unit comprises more than 90% methyl nonadienoates.

When the above described dimeric carbonylation of 1,3-butadiene reaction system is conducted with tri-secondary-butylphosphine as the ligand instead of triisobutylphosphine, a 90% selectivity of 1,3-butadiene to methyl nonadienoates is obtained at a rate of 64 grams per hour.

When triisobutylphosphine is employed as the ligand, the conversion selectivity of 1,3-butadiene to methyl nonadienoates is 89% at a rate of 63 grams per hour.

If tri-n-butylphosphine or tri-n-propylphosphine is employed as the ligand, the initial reaction rate is too low for continuous operation.

In the practice of the above-described dimeric carbonylation system, it is necessary to exclude the presence of halide contamination in order to minimize the production of methyl pentenoates, as well as to exclude catalyst poisons such as sulfur, selenium and tellurium which affect the conversion rate and selectivity of the process. Rigorous exclusion of molecular oxygen is also essential in order to prevent conversion of phosphine to phosphine oxide.

What is claimed is:

1. A process for producing and recovering alkyl nonadienoate which comprises the steps of (1) reacting 1,3-butadiene with carbon monoxide and a water-soluble alkanol containing between about 0.5–10 weight percent of water, in the presence of a catalyst complex of palladium and tertiary phosphine ligand, to yield a liquid phase product mixture containing alkyl nonadienoate; (2) contacting the product mixture with a hydrocarbon solvent to form two liquid phases; and (3) separating the two liquid phases, and recovering alkyl nonadienoate from the hydrocarbon solvent phase.

2. A process in accordance with claim 1 wherein the tertiary phosphine ligand has a $\Delta$HNP between about 70–350, and a steric parameter $\theta$ between about 136°–190°.

3. A process for producing and recovering alkyl nonadienoate which comprises the steps of (1) reacting 1,3-butadiene with at least molar equivalents of carbon monoxide and water-soluble alkanol in the presence of a hydrocarbon solvent and a catalytic quantity of a complex of palladium and tertiary phosphine ligand, at a temperature between about 30° C. and 150° C. and a pressure between about 200 and 3000 psi, to yield a reaction mixture containing alkyl nonadienoate; (2) adjusting the relative quantities of hydrocarbon solvent and alkanol in the reaction mixture, and adding water as required, sufficient to provide a hydrocarbon solvent phase and an alkanol phase containing between about 0.5–10 percent of water; and (3) separating the two phases and recovering alkyl nonadienoate from the hydrocarbon solvent phase.

4. A process in accordance with claim 3 wherein the dimeric carbonylation of the 1,3-butadiene proceeds in a substantially homogeneous liquid phase reaction medium.

5. A process in accordance with claim 3 wherein the water-soluble alkanol contains between 1 and about 5 carbon atoms and between 1 and about 4 hydroxyl groups.

6. A process in accordance with claim 3 wherein the water-soluble alkanol is methanol.

7. A process in accordance with claim 3 wherein the water-soluble alkanol is ethanol.

8. A process in accordance with claim 3 wherein the water-soluble alkanol is ethylene glycol.

9. A process in accordance with claim 3 wherein the water-soluble alkanol is 1,4-butanediol.

10. A process in accordance with claim 3 wherein the water-soluble alkanol is pentaerythritol.

11. A process in accordance with claim 3 wherein the hydrocarbon solvent is selected from acyclic and cyclic paraffins containing between 3 and about 8 carbon atoms.

12. A process in accordance with claim 3 wherein the molar ratio of butadiene to catalyst complex of palladium and tertiary phosphine ligand is at least 25:1.

13. A process in accordance with claim 3 wherein the palladium and tertiary phosphine ligand in the reaction medium are in a ratio between about 2–8 moles of tertiary phosphine ligand per gram atom of palladium metal.

14. A process in accordance with claim 3 wherein the tertiary phosphine ligand is trialkylphosphine.

15. A process in accordance with claim 14 wherein the trialkylphosphine is triisopropylphosphine.

16. A process in accordance with claim 14 wherein the trialkylphosphine is tri-n-butylphosphine.

17. A process in accordance with claim 14 wherein the trialkylphosphine is triisobutylphosphine.

18. A process in accordance with claim 14 wherein the trialkylphosphine is tri-secondary-butylphosphine.

19. A process in accordance with claim 3 wherein the tertiary phosphine ligand in the catalyst complex comprises between about 70 and 99 mole percent trialkylphosphine and between about 1 and 30 mole percent triarylphosphine.

20. A process in accordance with claim 19 wherein the trialkylphosphine is triisopropylphosphine and the triarylphosphine is triphenylphosphine.

21. A process in accordance with claim 3 wherein a vinyl polymerization inhibitor is present in the step (1) reaction medium.

22. A process in accordance with claim 3 wherein the tertiary phosphine ligand has a $\Delta$HNP between about 70–350, and a steric parameter $\theta$ between about 136°–190°.

23. A process in accordance with claim 3 wherein the separate alkanol phase recovered in step (3) is recycled in the process.

24. A process in accordance with claim 23 wherein the alkanol phase is extracted with hydrocarbon solvent to remove residual alkyl nonadienoate before the alkanol phase is recycled in the process.

25. A process in accordance with claim 3 wherein the hydrocarbon solvent recovered in step (3) is recycled in the process.

26. A process in accordance with claim 25 wherein the hydrocarbon solvent phase is extracted with water-soluble alkanol to remove residual catalyst complex before the respective alkyl nonadienoate and hydrocarbon solvent components of the hydrocarbon solvent phase are separately recovered, and the hydrocarbon solvent is recycled in the process.

27. A process in accordance with claim 3 wherein the conversion of 1,3-butadiene is at least 80 percent and the selectivity to alkyl nonadienoate and nonadienoic acid product is at least 80 mole percent.

28. A process in accordance with claim 3 wherein the alkyl nonadienoate product comprises a mixture of alkyl 3,8-nonadienoate and alkyl 2,8-nonadienoate.

29. A process in accordance with claim 28 wherein the molar ratio of alkyl 3,8-nonadienoate to alkyl 2,8-nonadienoate is at least 4:1.

30. A continuous process for producing and recovering alkyl nonadienoate which comprises the steps of (1) continuously charging and substantially filling an elongated reactor with a liquid phase reaction medium comprising water-soluble alkanol having a water content of between about 0.5–10 weight percent; (2) maintaining the reactor contents at a temperature between about 50° C. and 140° C. and under a partial pressure between about 100 and 1000 psi of carbon monoxide; (3) continuously introducing 1,3-butadiene and hydrocarbon solvent into the first end of the reactor; (4) continuously withdrawing hydrocarbon solvent as a separate phase from the second end of the reactor; (5) continuously separating alkyl nonadienoate product from the withdrawn hydrocarbon solvent phase; and (6) continuously recycling recovered hydrocarbon solvent to step (2) of the process.

31. A continuous process in accordance with claim 30 wherein the liquid phase reaction medium comprises a mixture of water-soluble alkanol and unreactive water-soluble diluent, and between about 0.5–10 weight percent of water, based on the total weight of the liquid phase reaction medium.

32. A continuous process in accordance with claim 30 wherein aqueous alkanol as a separate phase is continuously withdrawn from the second end of the reactor and recycled to step (1) of the process.

* * * * *